United States Patent [19]

Brown

[11] Patent Number: 4,712,951

[45] Date of Patent: Dec. 15, 1987

[54] TOOL FOR CUTTING ANNULAR GROOVE

[76] Inventor: Byron L. Brown, 2315 Hendrick Blvd., Fort Smith, Ark. 72903

[21] Appl. No.: 769,135

[22] Filed: Aug. 26, 1985

[51] Int. Cl.$^4$ .................. A61F 17/32; B23B 51/00
[52] U.S. Cl. .................. 408/158; 408/168; 408/169; 128/305; 82/1.2
[58] Field of Search .................. 128/305, 305.1, 310, 128/755, 757; 408/154, 156, 158, 165, 168, 169; 82/1.2

[56] References Cited

U.S. PATENT DOCUMENTS

| 79,276 | 6/1868 | Sullivan | 408/168 |
|---|---|---|---|
| 909,749 | 1/1909 | Brown et al. | 408/158 |
| 1,209,139 | 12/1916 | Gates | 408/158 |
| 2,333,935 | 11/1943 | Jones | 408/158 |
| 2,358,516 | 9/1944 | Knapp | 408/169 |
| 2,365,549 | 12/1944 | Haynes | 408/158 |
| 2,438,626 | 3/1948 | Strickland | 408/158 |
| 2,520,639 | 8/1950 | Johnson | 82/1.2 |
| 3,702,611 | 11/1972 | Fishbein | 128/305 |
| 4,271,849 | 6/1981 | Rehder | 128/305 |

FOREIGN PATENT DOCUMENTS

| 701188 | 12/1953 | United Kingdom | 408/168 |
|---|---|---|---|
| 1307512 | 2/1973 | United Kingdom | 408/154 |

Primary Examiner—Albert W. Davis, Jr.
Assistant Examiner—John K. Ford
Attorney, Agent, or Firm—Sigalos & Levine

[57] ABSTRACT

A tool for cutting an annular groove on the interior of a substantially cylindrical surface comprising a primary body having a pointed base for anchoring the cutting tool and a portion for being grasped and rotated by a power source, at least one groove cutting assembly attached to and extending horizontally from the primary body towards the internal cylindrical surface, and means coupled to said primary body and moveably spaced from the cutting assembly for selectively urging a portion of the cutting assembly outwardly a predetermined distance thereby enabling a groove of predetermined depth to be made on the interior of the interior cylindrical surface when the primary body is rotated.

10 Claims, 23 Drawing Figures

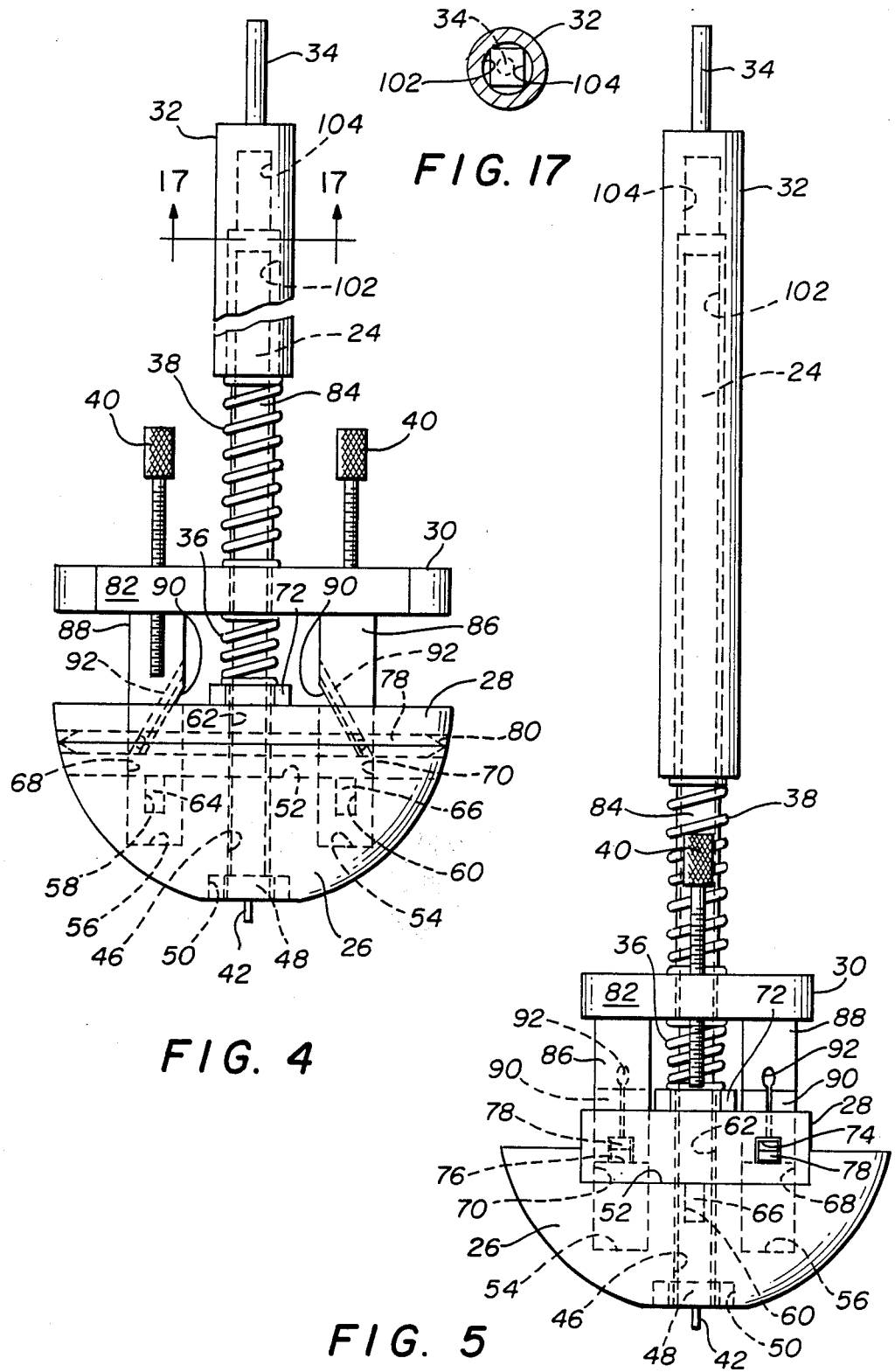

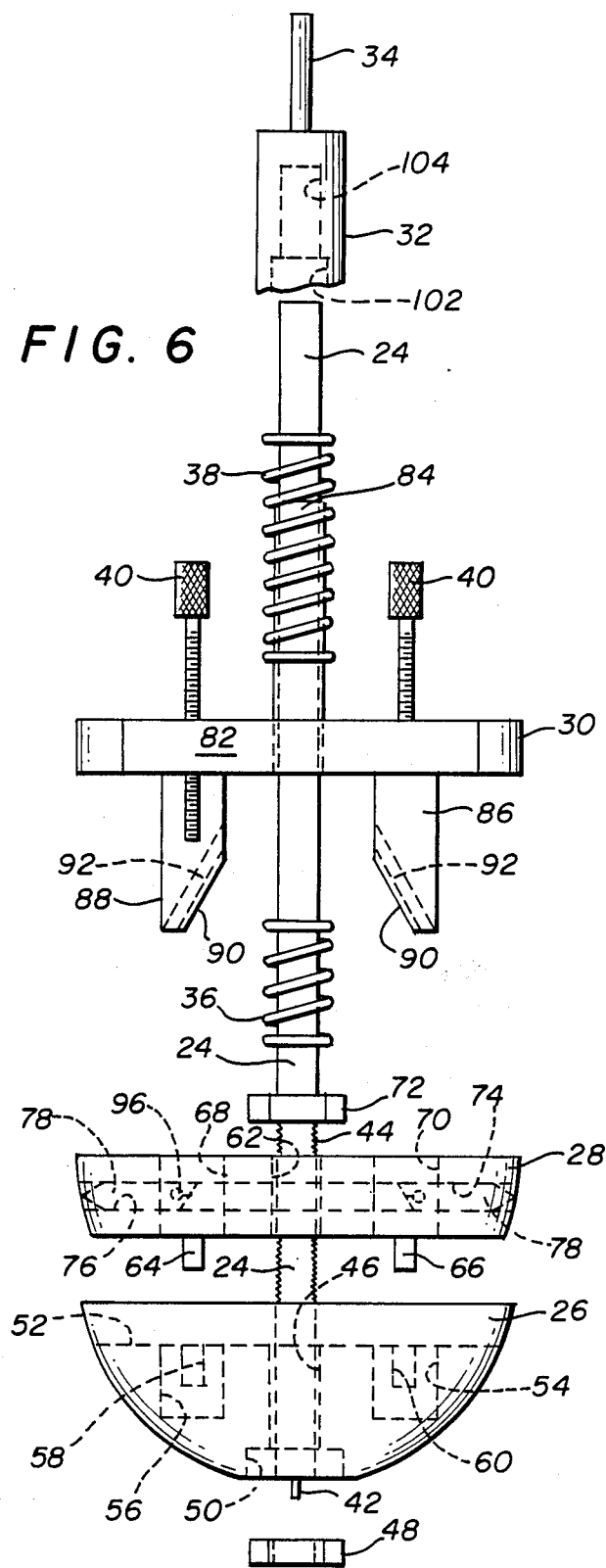
FIG. 6
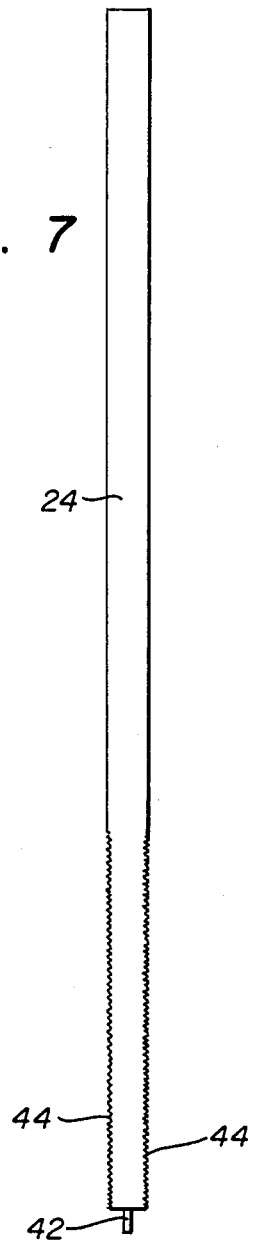
FIG. 7
FIG. 8

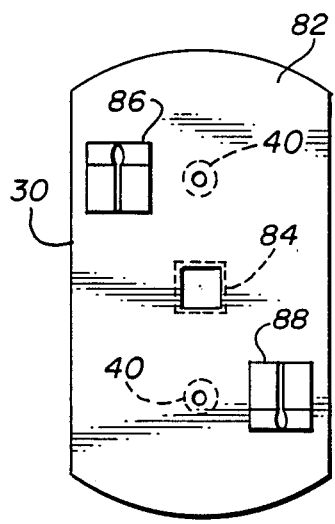
FIG. 16
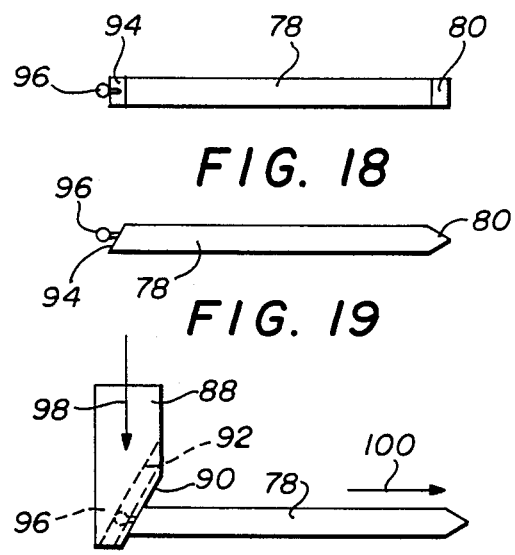
FIG. 18
FIG. 19
FIG. 20
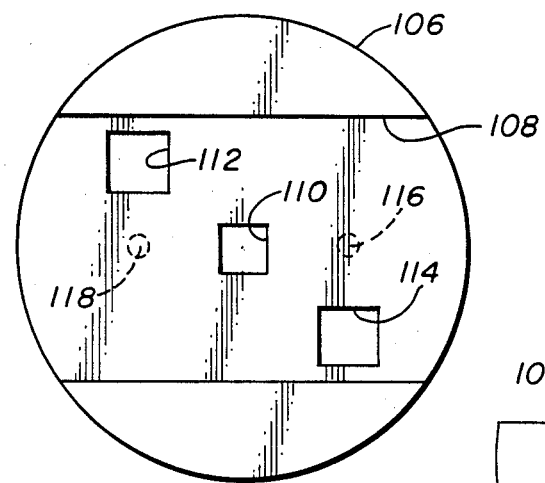
FIG. 21
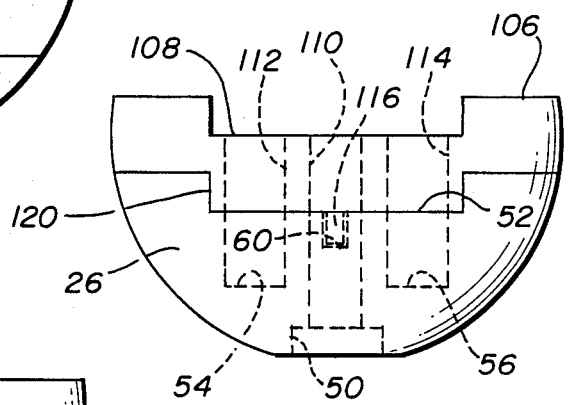
FIG. 23
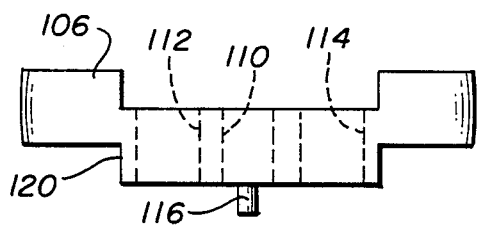
FIG. 22

TOOL FOR CUTTING ANNULAR GROOVE

BACKGROUND OF THE INVENTION

The present invention relates to a cutting tool and in particular to a tool for cutting an annular groove on the interior of a substantially cylindrical surface.

While this invention is suitable for cutting an annular groove on the interior of any substantially cylindrical surface, it will be discussed herein in particular in relationship to cutting an annular groove in the acetabulum of a body for preparation of the acetabulum socket to receive an acetabulum cup during hip replacement surgery. One of the greater problems of cement fixation of cup arthroplasty has been getting good fixation at the cement/bone interface. Several efforts have been made to improve this cement/bone interface. One method has used plastic spacers between the bony acetabulum and the plastic cup to allow an acceptable amount of cement to rest between the acetabulum and the cup. Other procedures have used surgically placed drill holes in the bony acetabulum and then the acetabulum and the drill holes are filled with cement of a doughy consistency. An acetabular cup is then inserted into the acetabulum and manual pressure is applied to the cup to force the cement between the trabeculae of the bone and into the drill holes. Other procedures utilize an acetabular cup having large screw threads on the outer periphery and the cup is actually threaded into the cup shaped acetabulum.

As described in copending patent application Ser. No. 748,856 filed June 26, 1985 and entitled Method and Apparatus for Cementing an Acetabular Cup to an Acetabulum, it was pointed out that after the acetabulum is prepared by using a first size reamer to remove the cartilage from the deepest portion of the acetabulum to form a spherical area in the weight bearing portion of the acetabulum and, where possible, by using a second, larger diameter reamer to remove the cartilage from the shallow portion of the acetabulum to form a second, larger spherical zone, that at least one annular groove can be formed at least in the spherical zone of the acetabulum about the inner periphery thereof to provide added fixation of the cement to the bone. Other annular grooves can be formed in the spherical zone and/or the spherical area of the acetabulum.

Thus, it is an object of the present invention to provide a tool for cutting an annular groove on the interior of a substantially cylindrical surface such as the spherical area or spherical zone of an acetabulum for receiving cement for enabling better cement/bone fixation.

It is another object of the present invention to provide a tool for cutting an annular groove on the interior of an acetabulum of predetermined depth.

It is still another object of the present invention to provide a tool for cutting annular grooves on the interior of the acetabulum at different diameters or elevations of the acetabulum.

SUMMARY OF THE INVENTION

Thus, the present invention relates to a tool for cutting an annular groove on the interior of a substantially cylindrical surface comprising a primary body having a pointed base for anchoring the cutting tool and a portion for being grasped and rotated by a power source, at least one groove cutting assembly, attached to and extending horizontally from said primary body toward said interior cylindrical surface and bias means coupled to said primary body and moveably spaced from said cutting assembly for urging a portion of said cutting assembly outwardly a predetermined distance thereby enabling a groove of predetermined depth to be made on said interior cylindrical surface when said primary body is rotated.

The invention also relates to a method of cutting annular grooves internal of an object comprising the steps of forming a primary body having a pointed base for anchoring said cutting tool and a portion for being grasped and rotated by a power source, attaching at least one groove cutting assembly to and extending horizontally from said primary body toward said interior cylindrical surface and urging a portion of said cutting element outwardly from said primary body a predetermined distance thereby enabling a groove of predetermined depth to be made on said interior cylindrical surface when said primary body is rotated.

BRIEF DESCRIPTION OF THE DRAWINGS

These and other objects of the present invention will be disclosed in conjunction with the specification and accompanying drawings in which:

FIG. 4 is a front view of the annular groove cutting tool of the present invention;

FIG. 5 is a side view of the annular groove cutting tool illustrated in FIG. 4;

FIG. 6 is an exploded front view of the annular groove cutting tool of the present invention illustrating the manner in which the various components are related to each other;

FIG. 7 is a front view of the central shaft of the present invention;

FIG. 8 is a bottom view of the central shaft shown in FIG. 7;

FIG. 16 is a bottom view of the wedge plate assembly shown in FIG. 14 and FIG. 15;

FIG. 17 is a cross-sectional view of the handle which couples the driving source to the annular groove cutting tool;

FIG. 18 is a top view of one of the annular cutting bits carried by the bit holder illustrated in FIG. 11 and FIG. 12;

FIG. 19 is a side view of the bit shown in FIG. 18 for cutting the annular grooves;

FIG. 20 is a side view illustrating how the bit shown in FIG. 18 and FIG. 19 for cutting the annular groove is slidably coupled to the wedge forming projection of the wedge plate illustrated in FIG. 14 to cause the bit to move into and out of the bony acetabulum for cutting the annular groove;

FIG. 21 is a top view of a spacing plate which may be placed on top of the hemispherical guide shown in FIG. 9 in order to change the vertical location within the acetabulum at which the annular groove should be cut;

FIG. 22 is a side view of the spacer illustrated in FIG. 21; and

FIG. 23 is a side view of the spacer attached to the hemispherical guide shown in FIG. 10 illustrating the manner in which the elevation of the annular groove within the acetabulum is raised with respect to the bottom of the acetabulum.

DETAILED DESCRIPTION OF THE DRAWINGS

Figure 1:
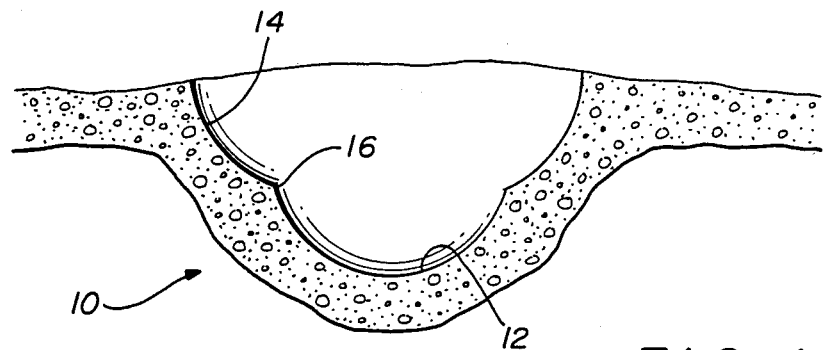
FIG. 1 is a cross-sectional view of the acetabulum after it has been prepared according to the procedures of the prior art.

FIG. 1 is a cross-sectional view of an acetabulum 10 that has been prepared to receive an acetabulum cup that is to be cemented therein. As can be seen in FIG. 1, the cartilage has been removed from spherical area 12 by using a first diameter reamer as disclosed in copending application Ser. No. 748,856 filed June 26, 1985 thus preserving the spherical area shape. In addition, cartilage from the shallow portion 14 of the acetabulum 10 has been removed with a second larger diameter reamer thus forming a larger spherical zone 14 and preserving at least a portion 16 of the cortical-like subchondrical bone structure at the juncture of the spherical area 12 and the spherical zone 14. It will be understood that with different types of acetabuli, it may not be possible to form both a spherical area 12 and the spherical zone 14 because of the shallow nature of a particular acetabulum. In that case, however, only one reamer is used to remove the cartilage from the acetabulum 10 and still maintain a single basically spherical shape in the acetabulum in order to provide a better and stronger weight bearing surface.

Figure 2:
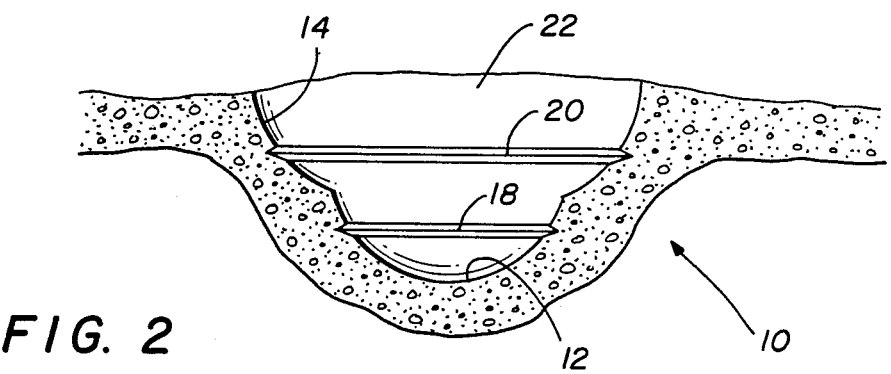
FIG. 2 illustrates a cross-sectional view of the prepared acetabulum shown in FIG. 1 and in which an annular groove has been formed in both the spherical area and the spherical zone of the acetabulum for receiving cement and in which the acetabular cup will be cemented.

FIG. 2 is a cross-sectional view of an acetabulum 10 in which a first annular groove 18 is formed in the spherical area 12 and a second annular groove 20 is formed in the spherical zone 14. These grooves 18 and 20 provide added fixation of the cement to the bone. Where it is not possible, because of the shape of a particular acetabulum, to form both a spherical area 12 and a spherical zone 14, then groove 20 should be placed in the shallow portion of the acetabulum 10. These annular grooves 18 and 20 are formed in a plane substantially parallel to the outer edge 22 of the spherical zone 14. Grooves 18 and 20, when filled with cement that hardens, produce a greater resistance to motion or loosening of the cement since a geometric circle structurally distributes stress substantially uniformly throughout the circle and thus has a relatively larger area of resistance than multiple small depressions filled with cement.

Figure 3:
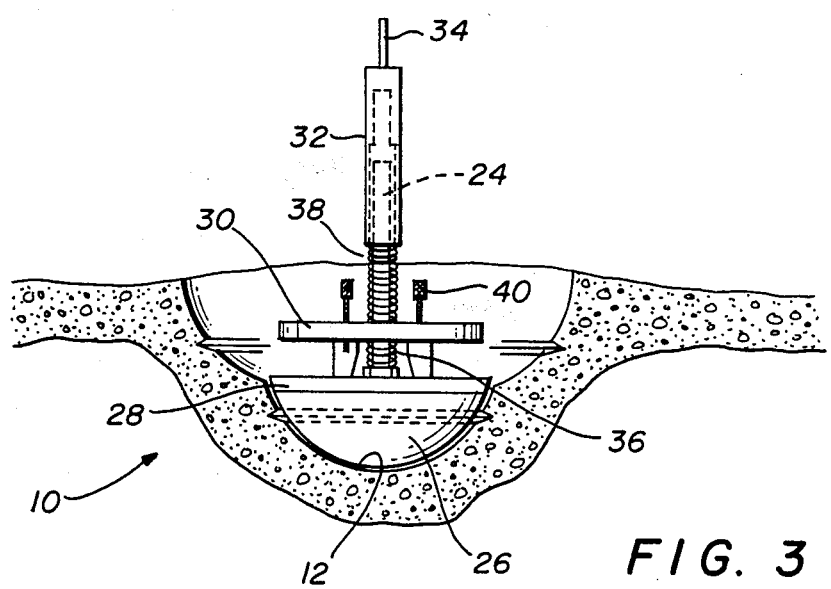
FIG. 3 is a cross sectional view of the acetabulum illustrating the manner in which the groove cutting tool of the present invention will be placed to form the annular groove in the spherical area of the acetabulum.
Figure 1:
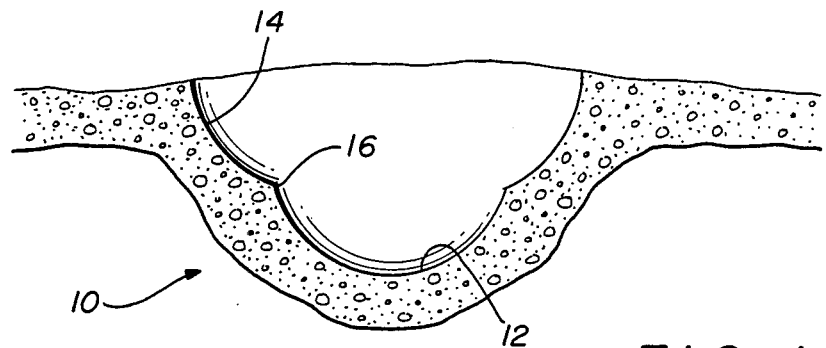
Figure 2:
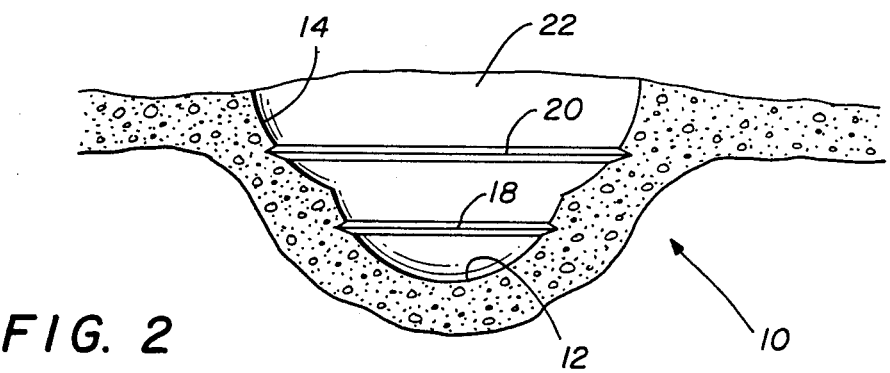
Figure 3:
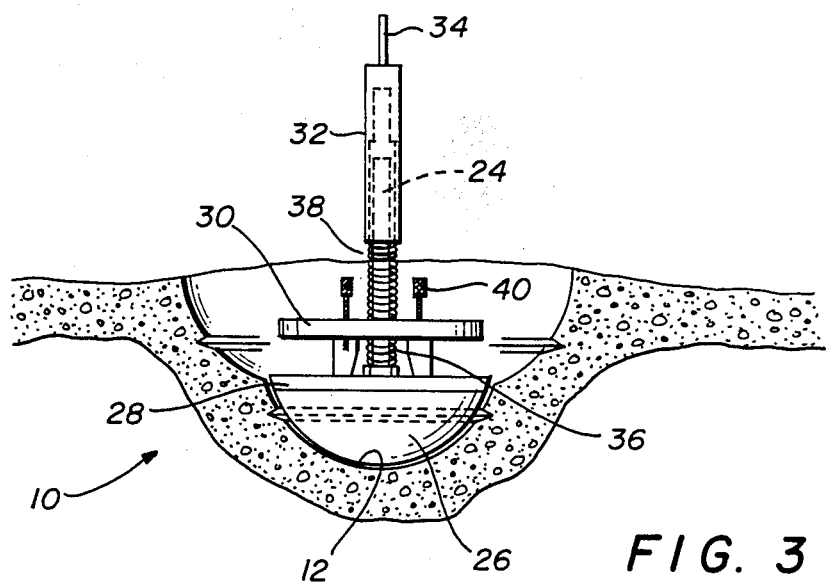

FIG. 3 illustrates an acetabulum 10 having the inventive tool of the present invention mounted therein for cutting the desired annular groove in the spherical area 12 of acetabulum 10. The tool comprises a primary body such as a central shaft 24 on the base of which is mounted a guide 26 having the shape of a spherical segment, but which will be designated hereinafter as a spherical guide, a groove cutting assembly including bit holder 28 which attaches to the spherical guide 26, extends horizontally from primary body or shaft 24 towards an interior cylindrical surface and which contains the bits for cutting the annular groove, a wedge plate 30 which, when pressed downwardly, gradually forces the cutting bits outwardly from the bit guide 28 to cut the desired annular groove as the spherical guide 26 rotates, a handle portion 32 having an extension or projection 34 on the outer end thereof for enabling a drill, ratchet or other rotating device to be attached thereto to rotate central shaft 24 and spherical guide 26 when downward pressure is applied thereto. A spring 36 forces wedge plate 30 upwardly thus retracting the cutting bits from the groove that has been cut after downward pressure is removed from handle 32. A second spring 38 enables the downward forces to be applied gradually to force cutting bits out of bit holder 28 to cut the desired annular groove. Set screws 40 adjust the length of the downward travel path of wedge plate 30 thus determining the depth of the annular groove that will be cut by the bits which are forced outwardly as wedge plate 30 is moved downwardly.

FIG. 4 and FIG. 5 are front and side views respectively of the tool for cutting the annular grooves in the acetabulum and FIG. 6 is an exploded representation of the front view of the tool shown in FIG. 4. Thus as can be seen in FIG. 4, FIG. 5 and FIG. 6, a primary body or central shaft 24 has mounted thereon spherical guide 26, bit holder 28, wedge plate 30 and handle 32.

Central shaft 24 is shown in detail in FIG. 7 and in FIG. 8 and comprises an elongated shaft having a square cross-section with threads 44 formed on the four corners thereof a partial distance along shaft 24 and has a sharp point 42 on the base thereof.

Figure 9:
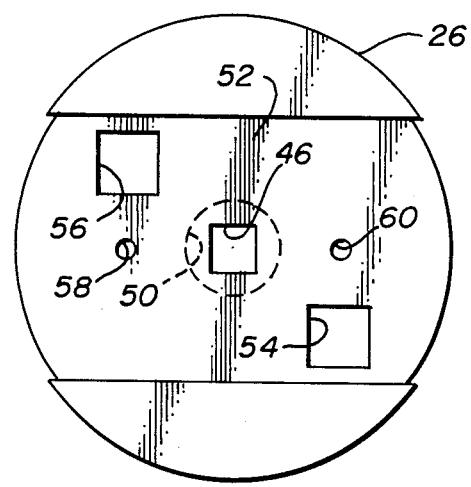
FIG. 9 is a top view of the hemispherical guide.
Figure 10:
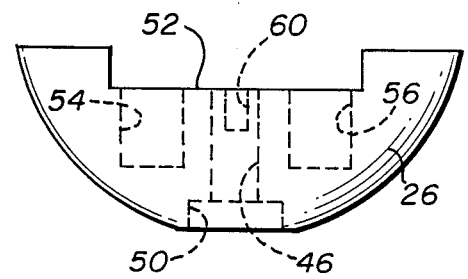
FIG. 10 is a side view of the hemispherical guide illustrated in FIG. 9.

Spherical guide 26 has a central square orifice 46 which can be seen more clearly in FIG. 9 and FIG. 10 through which central shaft 24 is inserted. A nut 48 is threaded onto the base of shaft 24 on threads 44 until it is positioned in recess 50 in the base of spherical guide 26. Guide 26 also has a notch 52 cut therein in which are formed additional recesses 54 and 56 for purposes which will be explained more fully hereafter with respect to wedge plate 30. In addition, orifices 58 and 60 are used to receive projections 64 and 66 from the bit holder 28 shown in FIG. 11 and FIG. 12 or projections 116 and 118 on a spacer 106 shown in FIGS. 21, 22 and 23 if it is desired to make the annular groove at a different elevation in the acetabulum 10.

Figure 12:
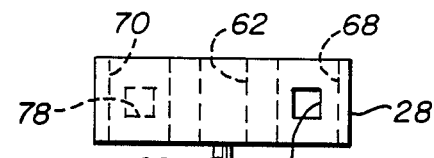
FIG. 12 is a side view of the cutting bit holder shown in FIG. 11.
Figure 11:
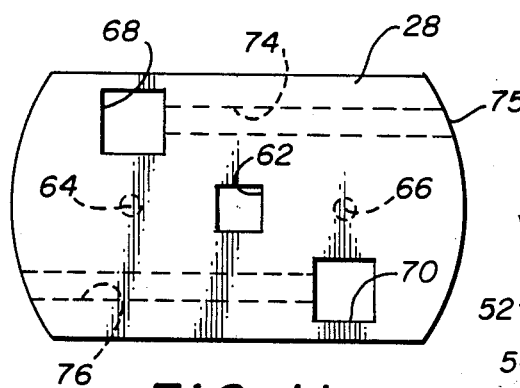
FIG. 11 is a top view of the cutting bit holder which carries the annular groove cutting bits.
Figure 13:
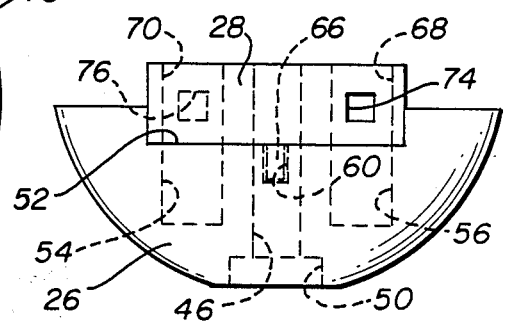
FIG. 13 illustrates the end view of the hemispherical guide shown in FIG. 10 with the cutting bit holder shown in FIG. 12 mounted therein.

Bit holder 28, which has a rectangular or square orifice 62 therein as shown in FIG. 11 and FIG. 12, is slipped over the top of central shaft 24 with central shaft 24 passing through orifice 62. As can be seen in FIG. 13, bit holder 28 is sized to fit notch 52 in spherical guide 26. Projections 64 and 66 from the underside of bit holder 28 mate respectively with orifices 58 and 60 of guide 26 (as shown in FIG. 9) to form a unitary element as shown in FIG. 13. Orifices 68 and 70 shown in FIG. 11 and FIG. 12 extend through bit holder 28 and also abut and are congruent with orifices 56 and 54 of guide 26 respectively as illustrated in FIG. 9. Nut 72 as seen in FIG. 4, FIG. 5 and FIG. 6, is now threaded on central shaft 24 and is tightened to hold bit holder 28 in fixed relationship with guide 26 as shown in FIG. 13. Horizontal bit passages 74 and 76 are formed in bit holder 28 with passageway 74 conmunicating with orifice 68 and passageway 76 communicating with orifice 70 as can be seen in FIG. 9. Bits 78, shown in FIG. 18 and FIG. 19, are placed in passages 74 and 76 such that the bit cutting portion 80 may be forced outwardly from the outer end of passages 74 and 76. Thus, cutting bit 78 can move outwardly or inwardly in passages 74 and 76.

Spring 36 is then placed over the outer end of central shaft 24 until it rests on nut 72. This spring 36 is to force wedge plate 30 away from bit holder 28 once the downward pressure has been removed as will be described in more detail hereinafter. The spring may vary in size or tension as needed.

Figure 15:
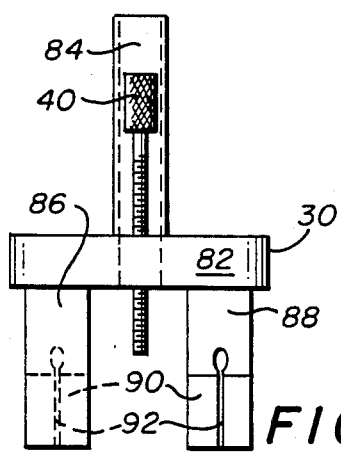
FIG. 15 is a side view of the wedge plate assembly shown in FIG. 14.
Figure 14:
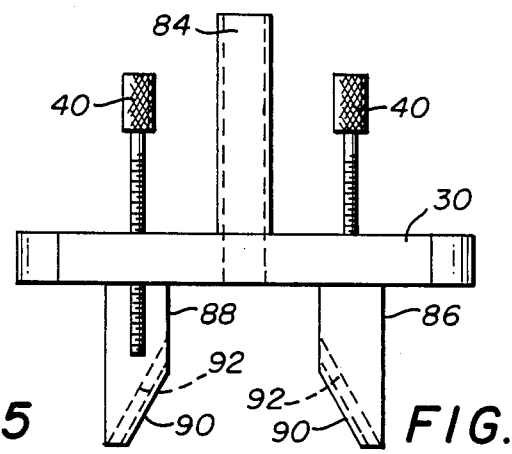
FIG. 14 is a front view of the wedge plate assembly.

Wedge plate 30 is shown in detail in the front view of FIG. 14, side view of FIG. 15, and bottom view of FIG. 16. Wedge plate 30 comprises a base 82 having integrally formed therewith a vertical duct or passage 84 with a rectangular or square cross-section for receiving central shaft 24. Depending therefrom are two wedge shaped projections or blocks 86 and 88 for moving downwardly in orifices 70 and 68 respectively and engaging a bit 78 and causing it to move inwardly and outwardly in passageways 74 and 76 in bit holder 28. Each of the wedge blocks 86 and 88 contain a sloping wedge shaped surface 90 having a circular channel or passageway 92 therein parallel to and communicating with said wedge shaped surface 90 for engaging the bit 78. The wedge shaped surface 90 urges the bits 78 to move inwardly and outwardly in their respective shafts 74 and 76 depending upon the direction of movement of the wedge blocks 86 and 88.

As can be seen in FIG. 18 and FIG. 19, bit 78 has a surface 94 on the base thereof that is wedge shaped to match the wedge shaped surface 90 of wedge blocks 86 and 88 for sliding attachment. Projecting from the wedge shaped surface 94 of cutting bit 78 is a ball 96 which engages and is inserted in channel or passageway 92 in the wedge blocks 86 and 88 as shown in FIG. 20 thus slidably attaching bit 78 to wedge block 86 and 88. As can be seen in FIG. 20, if wedge block 88 is pressed downwardly in the direction of arrow 98, sloping surface 94 of cutting bit 78 will slide against sloping surface 90 of wedge block 88 causing cutting bit 78 to be forced to the right as indicated by the direction of arrow 100. If it is assumed that cutting bit 78 is in passageway 74 shown in FIG. 11 and wedge block 88 is moving downwardly through orifice 68, and if the cutting bit 78 has slidably engaged wedge block 88 such that the tip of the cutting bit 78 is at the outer edge 75 of passage 74 in bit holder 28, as wedge block 88 is pushed downwardly into the plane of FIG. 11, bit 78 will begin to move to the right in FIG. 11 thus emerging from the outer end 75 of passageway 74 in bit holder 28 and exposing cutting edge 80 which can begin to cut an annular groove in the wall of the acetabulum 10 as the spherical guide 26 and attached bit holder 28 rotate. Thus, the further wedge plate 30 is pressed downwardly the further wedge blocks 86 and 88 move downwardly to cause cutting bit 78 to move outwardly from bit holder 28 thereby cutting the annular groove in the wall of acetabulum 10 as guide 26 and attached bit holder 28 rotate.

In order to limit or regulate the depth of the groove which is being cut, arms such as screws 40 are threadedly engaged with wedge plate 30 and extend therethrough so that the further screws 40 are threaded into wedge plate 30, the further they protrude from the bottom and the sooner they come in contact with bit holder 28 thus limiting any further downward movement of wedge plate 30 and its wedge blocks 86 and 88.

Thus, by regulating the point at which screws 40 contact bit holder 28, the depth of the annular groove can be adjusted. As wedge plate 30 is forced downwardly, spring 36 is compressed. When the downward force is removed, spring 36 tends to cause wedge plate 30 to move away from bit carrier 28 and the cutting bits 78 are withdrawn from the groove allowing the groove cutting tool to be removed from the acetabulum 10.

It will be understood that with sharp point 42 on the base of central shaft 24 as seen in FIG. 7 and FIG. 8, it will penetrate the bone structure of the acetabulum 10 and provide a solid fixation point for the groove cutting tool. In addition, the spherical shape of spherical guide 26 closely approximates the shape of the reamed spherical area of the acetabulum thus resisting side to side movement of central shaft 24 and providing further stability in holding the tool in a fixed position in the acetabulum thereby obtaining a horizontal annular groove of uniform cross-section about the inner surface of the acetabulum 10. Also, elongated duct 84 extending vertically and upwardly from wedge plate 30 and encircling shaft 24 also provides additional stability for central shaft 24 and tends to hold it in the vertical position and prevent it from having any slight movements to the side during rotation thereof thus further stabilizing the tool and further assuring that the annular grooves are substantially horizontal and of uniform cross-section.

Spring 38 is then placed over the end of central shaft 24 and encircles the vertically and upwardly extending duct 84 forming part of wedge plate 30. The purpose of this spring 38 is to provide a force against which handle 32 can be directed to allow controlled pressure to be applied gradually rather than abruptly to wedge plate 30. In addition, the spring 38 tends to force handle 32 upwardly after pressure is relieved from handle 32. The size or tension of this spring may be varied as needed to adapt to varying degrees of hardness of the bone.

As can be seen in FIG. 17, which is a cross-section of handle 32, handle 32 has a first hollow annular portion 102 which is larger than central shaft 24 allowing freedom of rotational movement of central shaft 24 within that portion of the handle 32. However, a second hollow rectangular or square passageway 104 is formed in the remainder of the handle 32. Thus, when handle 32 is resting on spring 38, it can freely rotate with respect to the rest of the annular groove cutting tool thus allowing the tool to be positioned and manipulated while being placed within the acetabulum 10. Once, however, pressure is applied to handle 32 downwardly against spring 38, central shaft 24 enters and engages the rectangular portion 104 of handle 32 thus locking handle 32 securely to central shaft 24 so that upon rotation of handle 32 central shaft 24 also rotates thus rotating the entire cutting tool. The bits 78 are caused to be forced outwardly against the inner circumference of the acetabulum 10 to cut the annular grooves as the pressure on the handle is applied downwardly against wedge plate 30 forcing wedge blocks 86 and 88 downwardly into passageways 68 and 70 of bit holder 28 thus forcing the bit 78 outwardly into the bony surface of the acetabulum 10 to cut a groove as the tool rotates.

Obviously, different size or diameter spherical guides 26 and different size mating bit holders 28 will be available to form annular grooves in different size acetabuli. In addition, if it is necessary to form an annular groove in the upper spherical zone of the acetabulum 10, the desired elevation of the annular groove can be obtained by adding spacing elements between the spherical guide 26 and the bit holder 28. Thus, as can be seen in FIG. 21, which is a top view of such a spacer 106, a recession 108 is formed therein for receiving the bit carrier 28. The recession 108 also includes a center orifice 110 through which the central shaft 24 can be inserted, and orifices 112 and 114 which abut and are in alignment with orifices 56 and 54 respectively of spherical guide 26 to receive the wedge blocks 88 and 86 as they extend down into bit carrier 28. Spacer 106 also has a lower extending projection 120 which can be inserted in notch or depression 52 in spherical guide 26. Projecting pins 116 and 118 mate with corresponding orifices 60 and 58 also in the spherical guide 26. Thus, as can be seen in FIG. 23, by mating spacer 106 with the spherical guide 26, the recession 108 in which the bit carrier 28 will be placed has been raised to a higher elevation thus raising the elevation at which the groove will be cut. Obviously, there can be different sizes and thicknesses of spacers 106 so that the bit carrier can be raised to any desired elevation. In addition, various sizes of spherical guide 26, bit carriers 28, bits 78, wedge plate 30, handle 32 and center shaft 24 may be used to accommodate different sizes of acetabuli.

Thus, there has been disclosed a novel tool for cutting an annular groove on the interior of a substantially cylindrical surface such as an acetabulum. As indicated, the tool may be utilized to cut an annular groove on the inner surface of any type of a cylindrical device; however, in this application the discussion has been limited to a process and apparatus for forming annular grooves in the acetabulum of a body for the purpose of obtaining a better cement/bone relationship in total hip replacements. The novel device allows different diameter annular grooves to be formed at different elevations within the cylindrical device. Further, a groove of predetermined depth is cut depending upon adjustments to limit the downward movement of the wedge plate to force the cutting bits outwardly into the acetabulum.

While the invention has been described in connection with a preferred embodiment, it is not intended to limit the scope of the invention to the particular form set forth, but, on the contrary, it is intended to cover such alternatives, modifications and equivalents as may be included within the spirit and scope of the invention as defined by the appended claims.

I claim:

1. A tool for cutting an annular groove on the interior of an annular surface comprising:
   a. a primary body having a pointed base for anchoring said cutting tool and a portion for being grasped and rotated by a power source, said portion of said primary body for being grasped and rotated by a power source comprises a handle having a first hollow portion forming means for positioning on and freely rotating about said primary body and a second hollow portion forming means for engaging said primary body wherein said body rotates with said handle, and a projection extending from the outer end of said handle for being grasped by said power source to rotate said primary body and cut said annular groove,
   b. a groove cutting assembly including a cutting bit carrier attached to and extending horizontally from said primary body towards said interior surface,
   c. at least one horizontal passageway in said bit carrier,
   d. a cutting bit slidably positioned in said horizontal passageway, said cutting bit including a cutting tip and a base,
   e. an orifice extending through said bit carrier perpendicular to and communicating with said cutting bit passageway,
   f. a wedge plate slidably attached to said primary body above said groove cutting assembly,
   g. a projection depending from said wedge plate and extending into said orifice in said bit carrier for movement upwardly and downwardly within said orifice,
   h. a sloping wedge shaped surface on said plate projection,
   i. a corresponding sloping wedge shaped surface on said base of said cutting bit for sliding attachment to said sloping wedge shaped surface on said plate projection so that said bit is moved outwardly when said projection is moved downwardly in said orifice and inwardly when said projection is moved upwardly in said orifice,
   j. a channel in said plate projection parallel to and communicating with said sloping wedge shaped surface of said plate projection,
   k. a mating projection on said wedge shaped sloping surface of said base of said cutting bit for insertion in said channel in said plate projection thereby slidably attaching said cutting bit to said plate projection,
   l. at least one arm mounted in and extending below said wedge plate toward and above said bit carrier and contacting said bit carrier as said wedge plate is forced downwardly to prevent further movement of said wedge plate,
   m. means for controlling the position of said one arm toward or away from said bit carrier thereby varying the downward travel of said wedge plate, and
   n. a spring positioned about said primary body and located between said wedge plate and said bit carrier to be compressed whem said wedge plate is moved towards said bit carrier thereby causing said wedge plate to be moved away from said bit carrier and said bit withdrawn from said groove when force on said wedge plate is removed.

2. A groove cutting tool as in claim 1 further including stabilizing means coupled to said primary body to enable horizontal annular grooves of substantial uniform cross-section to be cut in said interior annular surface.

3. A groove cutting tool as in claim 2 wherein said stabilizing means comprise:
   a. a guide attached to the base of said primary body and shaped to fit the interior of said annular surface to resist side to side movement of said primary body, and
   b. an elongated vertical duct extending upwardly from said wedge plate and encircling said primary body in slidable contact whereby said primary body has a tendency to remain in a vertical position.

4. A groove cutting tool as in claim 3 further including a force absorbing spring encircling said primary body and said elongated vertical duct between and engaging said wedge plate and said handle whereby downward force on said handle is gradually applied to said wedge plate only through said spring thereby causing a controlled pressure to be applied to said wedge plate.

5. A groove cutting tool as in claim 4 further including:
- a. a spacer unit for removable placement between said cutting bit carrier and said base guide whereby said cutting bit can be adjusted in elevation thereby adjusting the elevation of said annular groove,
- b. a recession in the top side of said spacer unit conforming to and receiving said bit carrier, and
- c. a projection on the bottom of said spacer unit conforming to the slot in the top of said base guide for fixedly securing said spacer unit to said base guide.

6. A method for cutting an annular groove on the interior of an annular surface comprising the steps of:
- a. forming a cutting tool with a primary body having a pointed base for anchoring said cutting tool and a portion for being grasped and rotated by a power source,
- b. attaching a groove cutting assembly including a cutting bit carrier to and extending horizontally from said primary body towards said interior surface,
- c. forming at least one horizontal passageway in said bit carrier,
- d. slidably positioning a cutting bit in horizontal passageway, said cutting bit including a cutting tip and a base,
- e. extending an orifice through said bit carrier perpendicular to and in communication with said cutting bit passageway,
- f. slidably attaching a wedge plate to said primary body above said groove cutting assembly,
- g. extending a projection from said plate into said orifice in said bit carrier for movement upwardly and downwardly within said orifice,
- h. forming a sloping wedge shaped surface on said plate projection,
- i. forming a matching sloping wedge shaped surface on said base of said cutting bit for slidable attachment to said sloping wedge shaped surface on said plate projection such that said bit is moved outwardly when said plate projection is moved downwardly in said orifice and inwardly when said plate projection is moved upwardly in said orifice,
- j. forming a channel in said plate projection parallel to and communicating with said sloping wedge shaped surface of said plate projection,
- k. forming a mating projection on said wedge shaped sloping surface of said base of said cutting bit for insertion in said channel in said plate projection thereby slidably attaching said cutting bit to said plate projection,
- l. mounting at least one arm in and extending below said wedge plate toward and above said bit carrier and contacting said bit carrier as said wedge plate is forced downwardly to prevent further movement of said wedge plate,
- m. controlling the position of said arm toward or away from said bit carrier thereby varying the downward travel of said wedge plate,
- n. positioning a apring about said primary body and located between said wedge plate and said bit carrier to be compressed when said wedge plate is moved downward toward said bit carrier thereby causing said wedge plate to be moved away from said bit carrier and said bit withdrawn from said groove when force on said wedge plate is removed,
- o. positioning a handle having a first hollow portion positioned on and freely rotating about said primary body and a second hollow portion for engaging said primary body wherein said body rotates with said handle, and
- p. extending a projection from the outer end of said handle for being grasped by said power source to rotate said primary body and cut said annular groove.

7. A method as in claim 6 further including the step of coupling a stabilizing means to said primary body to enable horizontal annular grooves of substantial uniform cross-section to be cut in said interior annular surface.

8. A method as in claim 7 further comprising the step of:
- a. attaching a guide to the base of said primary body shaped to fit the interior of said cylindrical surface to resist side to side movement of said primary body, and
- b. extending an elongated vertical duct upwardly from said wedge plate and encircling said primary body in slidable contact whereby said primary body has a tendency to remain in a vertical position.

9. A method as in claim 8 further including the step of encircling a force absorbing spring about said primary body and said elongated vertical duct between and engaging said wedge plate and said handle whereby downward force on said handle is gradually applied to said wedge plate only through said spring thereby causing a controlled pressure to be applied to said wedge plate.

10. A method as in claim 9 further including the steps of:
- a. adjusting said cutting bit in elevation by placing a spacer unit between said cutting bit carrier and said base guide whereby the elevation of said annular groove may be adjusted,
- b. forming a recession in the top side of said spacer unit conforming to and receiving said bit carrier,
- c. forming a projection on the body of said spacer unit conforming to the slot in the top of said base guide for fixedly securing said spacer unit to said base guide.

* * * * *